United States Patent [19]

Garritano et al.

[11] Patent Number: 4,640,120
[45] Date of Patent: Feb. 3, 1987

[54] IMPACT TESTING APPARATUS

[75] Inventors: Ronald F. Garritano, Flemington; John J. O'Connor, Roselle Park; Manuel E. Papayanopulos, Elizabeth, all of N.J.

[73] Assignee: Rheometrics, Inc., Piscataway, N.J.

[21] Appl. No.: 747,646

[22] Filed: Jun. 21, 1985

[51] Int. Cl.[4] .............................................. G01N 3/30
[52] U.S. Cl. ...................................................... 73/12
[58] Field of Search ...................... 73/12, 82, 839, 844

[56] References Cited

U.S. PATENT DOCUMENTS 2,740,286  4/1956  DeVost et al. ........................... 73/12

FOREIGN PATENT DOCUMENTS 1104953  3/1968  United Kingdom ..................... 73/12
0606121  5/1978  U.S.S.R. .................................... 73/12

OTHER PUBLICATIONS

Bityutskii et al, "Vertical Impact Testing Machine . . . Rubber Accelerator", Industrial Laboratory, vol. 41, No. 8, Aug. 1975, pp. 1277-1278.
Kostrov et al., "Spring Device for Impact Tests of Plastics", Ind. Lab., vol. 45, No. 11, Nov. 1979, pp. 1305-1306.
Stalevich et al, "Apparatus for Determining the Shear Impact Strength . . . ", Meas. Tech., No. 6, Jun. 1970, pp. 860-862.

Primary Examiner—Charles A. Ruehl
Attorney, Agent, or Firm—Samuelson & Jacob

[57] ABSTRACT

Impact testing apparatus in which a weighted dart is dropped from a prescribed height to penetrate a test specimen when traveling at a desired velocity and level of kinetic energy, the acceleration of the dart being assisted by a spring force in the direction of travel so that the prescribed height is maintained at a minimum for a given desired velocity and the dart being guided to the test specimen by a generally tubular guide within which the dart is loosely fitted. A force transducer is located at the tip of the dart for providing impact force information as the tip penetrates the test specimen.

25 Claims, 6 Drawing Figures

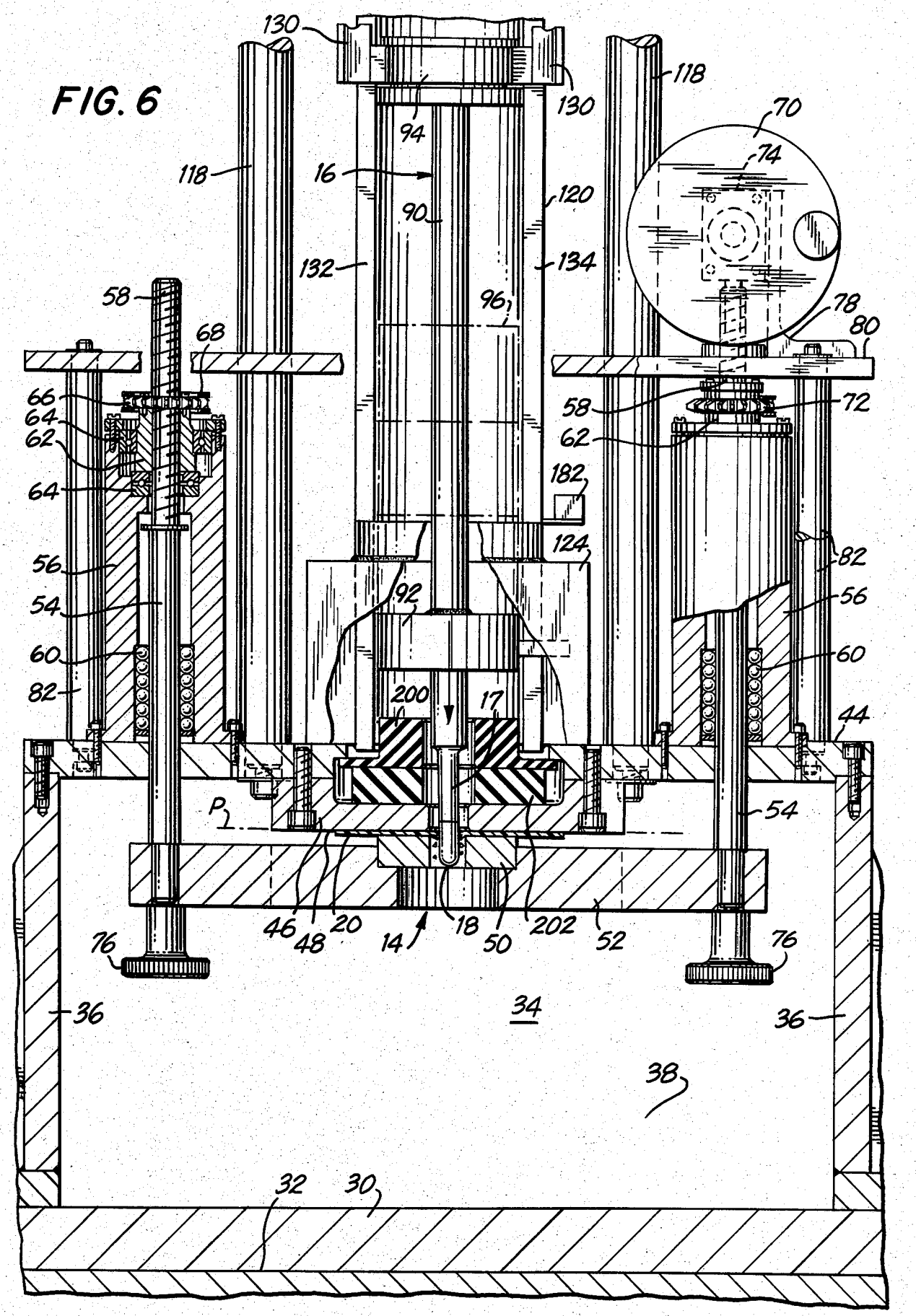

IMPACT TESTING APPARATUS

The present invention relates generally to materials testing and pertains, more particularly, to apparatus for determining the impact strength characteristics of sheet-like materials ranging from rigid composite panels to relatively thin films.

The increased demand for more and varied materials tailored for specific end uses has required that materials testing techniques and apparatus be developed to meet the need for testing devices which not only are capable of dealing with a wide range of materials with ease of use and with accuracy, but which are compact and economical enough to be used in a variety of workplaces where the use of such equipment is desirable, but heretofore has been impractical. The testing of various materials for impact strength has been carried out in the past utilizing a variety of techniques. The present apparatus improves upon techniques and devices of the type in which a weighted object is dropped upon a test specimen to examine the response of the specimen to impact.

It is an object of the present invention to provide impact testing apparatus capable of eliciting useful data from the testing of a wide range of materials, from relatively thick and rigid panels to relatively thin films, in a variety of compositions.

Another object of the invention is to provide impact testing apparatus of the type described and which is relatively compact, for installation in facilities where devices of such range heretofore have been unavailable.

Still another object of the invention is to provide impact testing apparatus of the type described and which attains data of increased variety and accuracy for more meaningful results.

Yet another object of the invention is to provide impact testing apparatus of the type described and which is easy to use, enabling widespread utilization by less skilled operators, with enhanced results.

A further object of the invention is to provide impact testing apparatus of the type described and which enables increased versatility for obtaining useful data over a wide variety of conditions.

A still further object of the invention is to provide impact testing apparatus of the type described and which is economical to manufacture while attaining increased versatility and accuracy.

The above objects, as well as still further objects and advantages, are attained by the present invention which may be described briefly as an improvement in testing apparatus for determining impact characteristics of a test specimen placed at a prescribed location in a testing station, the test specimen being subjected to impact by a test element traveling under free-fall at a predetermined velocity and level of kinetic energy, the improvement comprising: holding means for holding the test specimen at the prescribed location in the testing station; impact means carrying the test element and moveable between a first position located at the testing station and a second position spaced above the testing station; elevating means for elevating the impact means and the test element from the first position to the second position to impart potential energy to the impact means related to the height of the second position above the first position; coupling means for coupling the impact means with the elevating means; supplemental energy-input means responsive to movement of the impact means beyond an intermediate position located between the first position and the second position, during movement of the impact means in the direction from the first position toward the second position to impart additional energy to the input means; guide means for guiding the impact means for elevation by the elevating means between the first position and the second position and for essentially free-fall between the intermediate position and the first position; and control means for determining the height of the second position above the first position and above the intermediate position, the height being determined by the total energy available to the impact means to provide the predetermined velocity and level of kinetic energy in the impact means at the testing station, the control means being coupled to the coupling means for operating the coupling means to release the impact means at the second position for downward movement and essentially free-fall between the intermediate position and the first position, whereby the test element will impact the test specimen during free-fall and at the desired predetermined velocity and level of kinetic energy.

The invention will be understood more fully, while still further objects and advantages will become apparent, in the following detailed description of a preferred embodiment illustrated in the accompanying drawing, in which:

FIG. 6 is an enlarged fragmentary view of a portion of the apparatus, similar to FIG. 2, but with component parts in another operating position.

Figure 1:
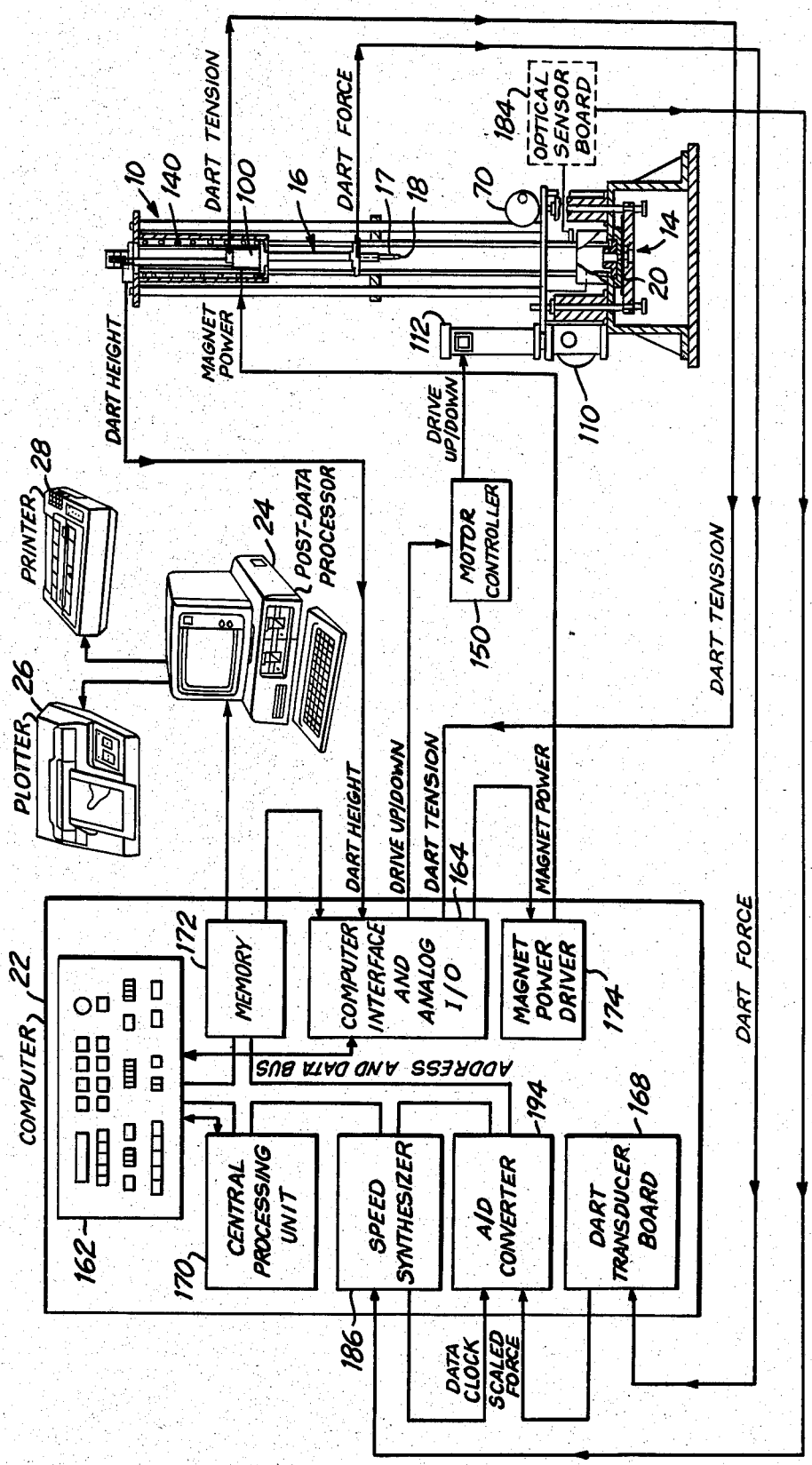
FIG. 1 is a diagrammatic illustration of an impact testing apparatus constructed in accordance with the present invention.

Referring now to the drawing, and especially to FIG. 1 thereof, an impact testing apparatus constructed in accordance with the invention is illustrated, generally diagrammatically, at 10. Apparatus 10 includes a main frame 12 within which there is located a test station 14. An impact device in the form of a dart 16 moves between a first or lower position, located at the test station 14, and a second or upper position, elevated above the test station, and carries an impact test element in the form of a probe-like member 17 having a distal tip 18 designed to penetrate a test specimen 20 secured in place in the test station 14. In this manner, the test data pertaining to the impact characteristics of the test specimen 20 is obtained, under the control of a computer 22, and is made available for utilization at a post-data processor 24 and ancillary data display devices such as a plotter 26 and a printer 28.

Figure 2:
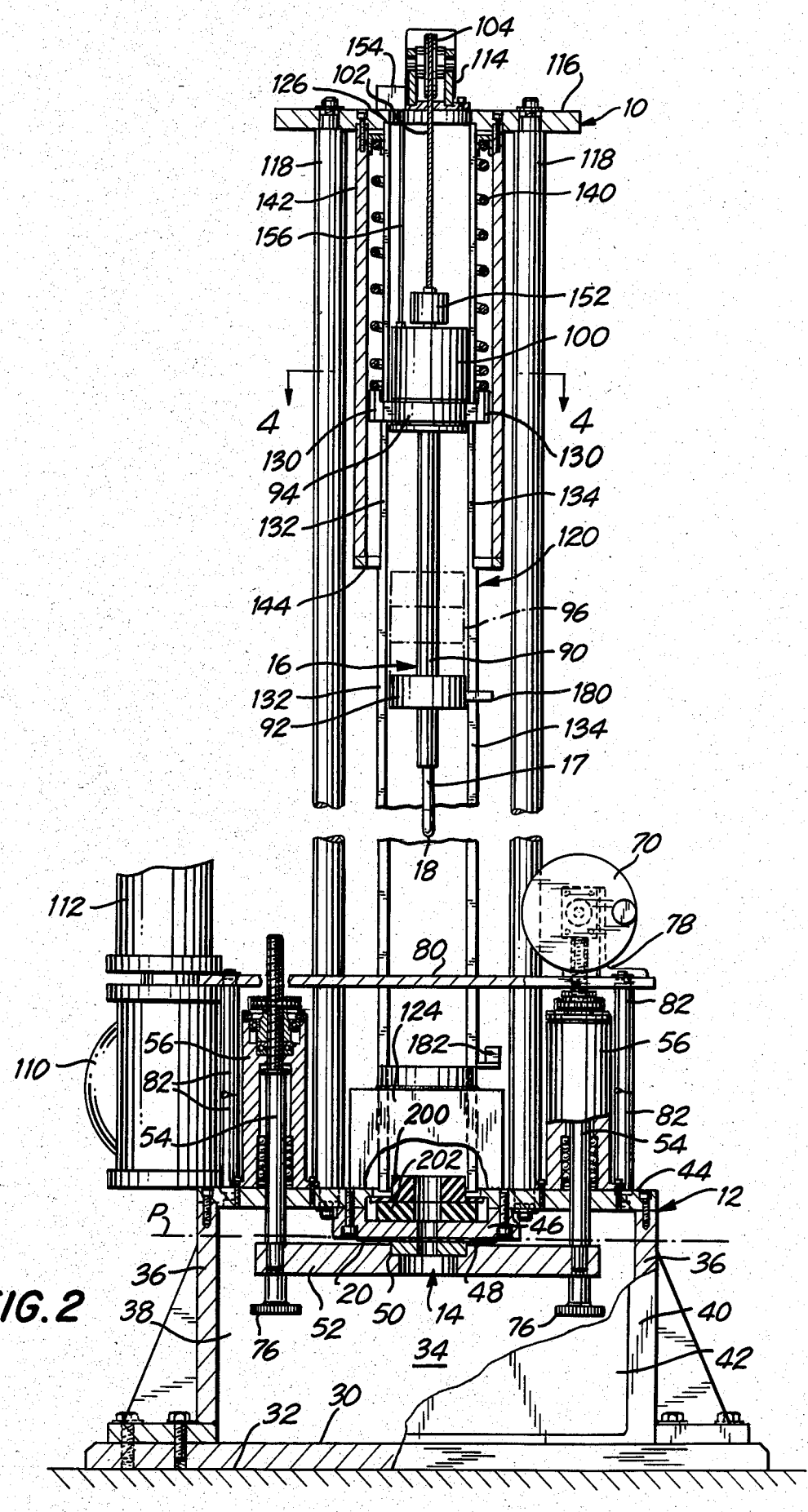
FIG. 2 is a front elevational view, partially sectioned, of the impact testing apparatus.

Turning now to FIG. 2, main frame 12 is secured to a base plate 30 which rests upon the floor 32 of the test facility. Test specimen 20 is enclosed within a chamber 34 established by side walls 36, a rear wall 38 and a front wall 40. Front wall 40 includes a door 42 which opens outwardly to enable access to the inside of chamber 34 so that test specimen 20 may be inserted and removed from the test station 14.

Frame 12 includes a platform 44 secured to the side walls 36 at the uppermost edges thereof (also see FIG. 6). A test pad 46 is affixed to the platform 44 and includes a lower surface 48 against which the test specimen 20 is placed. A clamping pad 50 is carried by a clamping plate 52 which is movable selectively in upward and downward directions to clamp and release test specimen 20. Lower surface 48 of test pad 46 is located in a test plane P, and clamping pad 50 is movable toward and way from test plane P so that regardless of the thickness of test specimen 20, the upper surface of the test specimen always is located at the fixed location of the test plane P.

Figure 3:
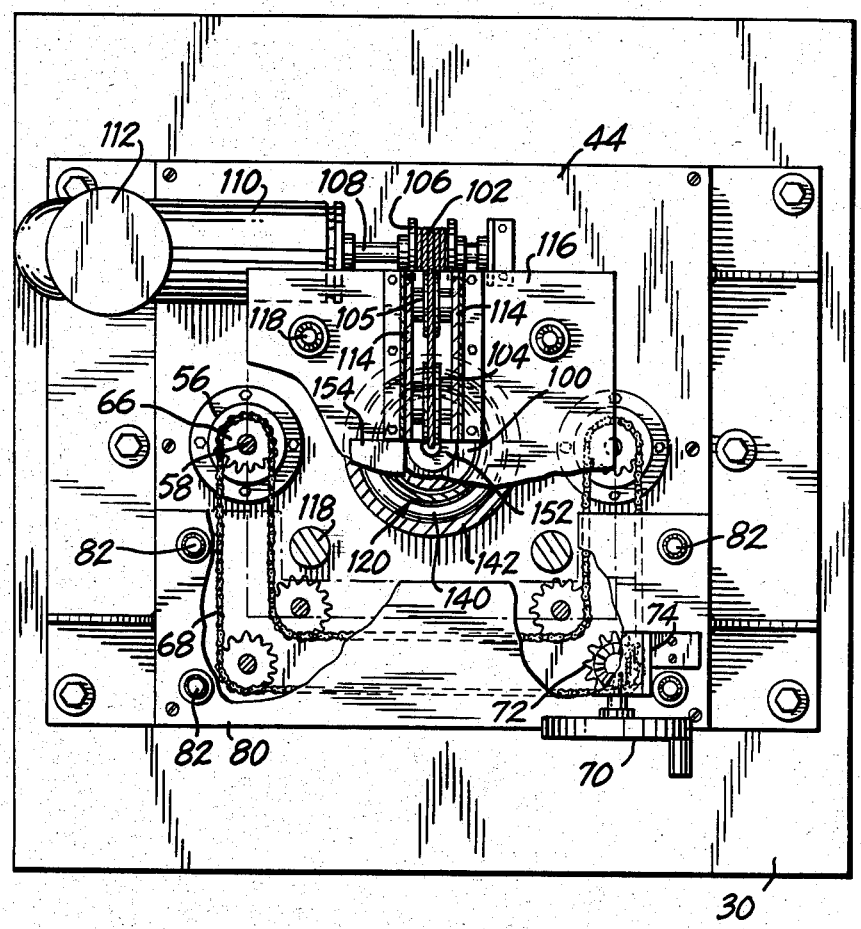
FIG. 3 is a top plan view of the apparatus, with portions broken away to illustrate internal details.
Figure 4:
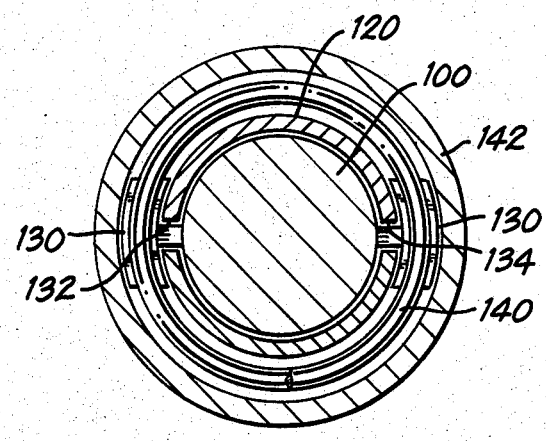
FIG. 4 is a fragmentary cross-sectional view taken along line 4—4 of FIG. 2.

To this end, clamping plate 52 is secured to rods 54 which extend upwardly through blocks 56 affixed to platform 44 and include externally threaded extensions 58 (also see FIG. 6). Rods 54 are moved upwardly or downwardly within bearings 60 by the rotation of internally threaded collars 62 fixed within blocks 56 at bearings 64. Sprockets 66 are engaged with collars 62 and, as also seen in FIG. 3, a drive chain 68 couples sprockets 66 with a handwheel 70, through a drive sprocket 72 and bevel gear drive 74, such that upon selective rotation of handwheel 70, clamping plate 52 and clamping pad 50 are moved into or out of clamping position in relation to test pad 46 to clamp a test specimen 20 of any one of a variety of thicknesses in place in the test station 14, with the upper surface of the test specimen placed in test plane P. Clamping plate 52 itself is easily removed and replaced by virtue of knobs 76 which are threaded onto the lower ends of rods 54 to secure clamping plate 52 in place. Handwheel 70 and bevel gear drive 74 are carried by a bracket 78 affixed to an upper platform 80 supported above lower platform 44 by spacers 82. The entire arrangement supports the test specimen 20 with strength and rigidity so as to withstand the impacts experienced during testing, as explained below.

Referring now to FIGS. 2 and 3, dart 16 includes a central shaft 90 extending axially between a lower flange 92 and an upper flange 94. A selected number of weights, shown in phantom at 96, may be placed on the dart 16, between the lower and upper flanges 92 and 94, to selectively increase the mass of the dart to a desired magnitude. Upper flange 94 preferably includes a ferrous material so that an electromagnet 100 can be coupled selectively to the dart 16 at the upper flange 94. Electromagnet 100 is secured to a cable 102 which extends around pulleys 104 and 105 and is upon a drum 106 carried by a drive shaft 108 driven by a gear drive 110 and motor 112 placed on the lower platform 44. Pulleys 104 and 105 are journaled for rotation in brackets 114 secured to an uppermost plate 116 supported by four columns 118 which extend between the uppermost plate 116 and the lower platform 44.

Dart 16 travels within a generally tubular guide 120 and is loosely fitted within guide 120, for purposes which will be explained in greater detail below. Guide 120 is supported upon lower platform 44 at support sleeve 124 and extends upwardly from the platform 44 to an upper end 126 secured within the uppermost plate 116. A pair of diametrically-opposed ears 130 are carried by the upper flange 94 of dart 16 and extend radially outwardly beyond the guide 120, the guide 120 being split longitudinally at slots 132 and 134 to provide clearance for the ears 130 as the dart 16 traverses the guide 120. The loose fit of the dart 16 within the split guide 120 enables generally unimpeded downward travel of the dart 16 within the guide, and essentially free-fall as the dart 16 reaches the test specimen 20, providing very smooth motion and reducing excited resonances to a minimum, as compared with multiple-bearing crosshead arrangements now in common use. Such a reduction in noise enables a much wider dynamic range for force measurements so that reliable test data can be obtained for rigid composite panel test specimens as well as for film test specimens.

The impact characteristics of test specimen 20 are to be tested by dropping dart 16 from an upper position located such that the energy in the downwardly falling dart 16 will be sufficient to enable the lower distal tip 18 of probe-like member 17 of the dart 16 to penetrate the test specimen 20. The energy available in the dart at the point of impact may be varied by adding mass to the dart, as described above. However, impact characteristics are dependent upon the velocity of the dart, as well, and velocity is related to the downward acceleration of the dart prior to impact. It is desirable to have available selected velocities up to about 30,000 inches per minute (IPM); however, to achieve such speeds by merely dropping dart 16 would require that the dart be dropped from a height of about twenty-seven feet above the test specimen. Since it is an object of the present invention to enable the utilization of apparatus 10 within the facilities offered by a room of ordinary dimensions, namely, a room having an eight-foot ceiling, apparatus 10 is provided with means for imparting added acceleration to dart 16 so that velocities as high as 30,000 IPM can be obtained within the confines of a drop height of something less than eight feet. Thus, a helical spring 140 is secured at its upper end to uppermost plate 116 and extends downwardly adjacent the outer perimeter of guide 120 so as to be intercepted by ears 130 as the dart 16 is raised. An outer tubular casing 142 is affixed to uppermost plate 116 and extends downwardly around the spring 140 to a lower end supported upon an annular support 144 so as to surround and encase the spring 140 for safety purposes.

Figure 5:
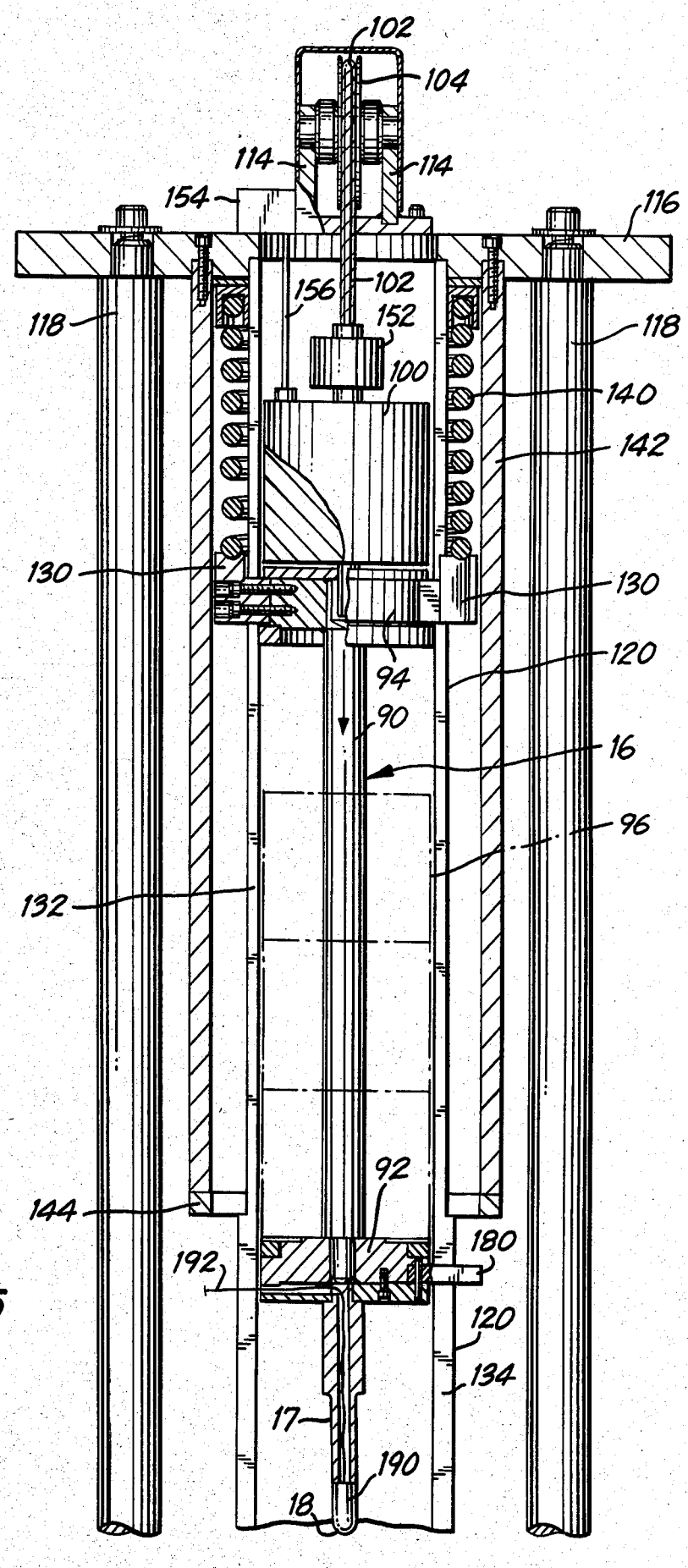
FIG. 5 is an enlarged fragmentary view of a portion of the apparatus, similar to FIG. 2.

As best seen in FIGS. 5 and 6, as well as in FIG. 2, dart 16 is raised by coupling electromagnet 100 with upper flange 94 and operating motor 112 to wind cable 102 upon drum 106. Motor 112 is operated under the control of motor controller 150 (see FIG. 1). As the dart 16 is raised above test plane P, the potential energy in dart 16 increases by virtue of the increased height above test plane P. At an intermediate position of the dart 16, between the lower position, where the tip 18 of the dart 16 is at test plane P, and the upper position, where the dart 16 will be released for downward movement, the ears 130 engage the spring 140 so that further upward movement compresses spring 140 to increase the total energy available in the dart 16 and spring 140 system. Upon reaching the upper position, where the total energy in the system is such that the dart will have the desired level of kinetic energy at the desired velocity when the dart has fallen to test plane P at test station 14, electromagnet 100 is deactivated and the dart is released for downward movement as shown by the arrow in FIG. 5. Initially, spring 140 will expand and accelerate the dart downwardly, and this acceleration together with the acceleration of gravity, will drive the dart 16 downwardly within the tubular guide 120. As the dart 16 moves downwardly beyond the intermediate position, toward the lower position, the dart will travel under essentially free-fall until tip 18 reaches the desired velocity at test plane P. The total energy in dart 16 will assure that the test specimen 20 is penetrated by the tip 18 of dart 16.

The location of the upper position of the dart 16 is determined by information received from a dart-tension transducer 152 interposed between cable 102 and electromagnet 100 so that transducer 152 provides a measure of the energy which will be imparted to dart 16 by spring 140, and a dart-height transducer 154 mounted upon uppermost plate 116 and coupled to the electromagnet 100 by a measuring strand 156 to provide information pertaining to the height of the dart 16 above test plane P. As seen in the diagrammatic illustration of FIG. 1, the dart-height information and the dart-tension information are utilized by control computer 22 to determine precisely the position where dart 16 must be released to obtain the desired energy and velocity at test plane P. Thus, an operator may input a desired velocity, energy or height at the control panel 162 of control computer 22. Dart height information is directed to a computer interface and analog I/O 164. Dart tension information also is brought to the computer interface and analog I/O 164. A central processing unit 170, working in conjunction with a memory 172, determines the appropriate location of the upper position of dart 16 and operates magnet power driver 174 to deactivate electromagnet 100, thereby dropping the dart 16 from the appropriate height and at the appropriate compression of spring 140. The arrangement provides an accurately calibrated means for determining precisely the position where the dart 16 must be released. Since the dart 16 is dropped by deactivating electromagnet 100, the release is smooth and certain, without any jolts or other mechanical distortions which can be introduced by mechanical release mechanisms.

As the dart 16 approaches test plane P, an optical flag 180 carried by the dart passes through an optical sensor 182 to measure the actual velocity of the dart 16 just prior to impact. Information from the optical sensor 182 is conditioned by an optical sensor board 184 and passed to a speed synthesizer 186 for use by the central processing unit 170 in providing precise impact information. As the probe-like member 17 impacts and penetrates the test specimen 20, as seen in FIG. 6, impact information is obtained from a force transducer 190 integral with the probe-like member 17 adjacent tip 18 of dart 16. Location of the force transducer 190 in the probe-like member 17 in juxtaposition with the tip 18 minimizes the mass placed between the transducer 190 and the test specimen 20, thereby reducing the effects of any resonances in the apparatus upon impact. Preferably, transducer 190 is a piezoelectric device and the information provided by the transducer 190 is made available at a lead 192 (see FIGS. 5 and 6). Information from transducer 190 is conditioned by a dart transducer board 168 and passed to a very high speed analog-to-digital converter 194. The impact force is sampled at approximately every thousandth of an inch of dart displacement. Impact data is then corrected for deceleration resulting from impact, using measured speed and the sampled force/time profile. Thus, the data stored in memory 172 is a true force/displacement record of the impact of dart 16 with the test specimen 20. The data in memory 172 then may be made available to the post-data processor 24 and any peripheral equipment such as plotter 26 and printer 28.

It will be seen that the arrangement of the test pad 44 and clamping pad 50 enable each to be replaced selectively with corresponding components of other configurations so that the impact area can be changed, as desired, for various test specimens. The thickness of the test specimen may vary without affecting the location of test plane P so that height measurements are not affected by varying the dimensions of the test specimen. Elastomeric pads 200 and 202 are provided to absorb the bulk of the energy remaining in the dart 16 after penetration of the probe-like member 17 through the test specimen 20 and after data acquisition when the lower flange 92 will contact the elastomeric pads 200 and 202 and the dart 16 will come to rest.

The chamber 34 enables the test specimen 20 to be enclosed both for safety purposes and for the purpose of providing a specific environment at test station 14, within which environment test specimen 20 is to be tested. For example, the temperature within chamber 34 can be controlled within a given range, as desired.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. In testing apparatus for determining impact characteristics of a test specimen placed at a prescribed location in a testing station, the test specimen being subjected to impact by a test element traveling under free-fall at a predetermined velocity and level of kinetic energy, the improvement comprising:
   holding means for holding the test specimen at the prescribed location in the testing station;
   impact means carrying said test element and moveable between a first position located at the testing station and a second position spaced above the testing station;
   elevating means for elevating the impact means and the test element from the first position to the second position to impart potential energy to the impact means related to the height of the second position above the first position;
   coupling means for coupling the impact means with the elevating means;
   supplemental energy-input means responsive to movement of the impact means beyond an intermediate position located between the first position and the second position, during movement of the impact means in the direction from the first position toward the second position to impart additional energy to the impact means;
   guide means for guiding the impact means for elevation by the elevating means between the first position and the second position and for essentially free-fall between the intermediate position and the first position; and
   control means for determining the height of the second position above the first position and above the intermediate position, said height being determined by the total energy available to the impact means to provide the predetermined velocity and level of kinetic energy in the impact means at the testing station, said control means being coupled to the coupling means for operating the coupling means to release the impact means at the second position for downward movement and essentially free-fall between the intermediate position and the first position, whereby the test element will impact the test specimen during free-fall and at the desired predetermined velocity and level of kinetic energy.

2. The invention of claim 1 wherein the test element comprises a probe-like member projecting downwardly to a distal tip for penetrating the test specimen upon said impact, and a force transducer juxtaposed with the distal tip.

3. The invention of claim 2 including data-acquisition means coupled with the force transducer for sampling information received from the force transducer as the distal tip penetrates the test specimen.

4. The invention of claim 2 wherein the impact means includes selective means for selectively varying the mass of the impact means to vary the level of kinetic energy available to the test element at the testing station.

5. The invention of claim 4 including data-acquisition means coupled with the force transducer for sampling information received from the force transducer as the distal tip penetrates the test specimen.

6. The invention of claim 1 wherein the coupling means includes an electromagnet for coupling the impact means with the elevating means.

7. The invention of claim 6 wherein the control means includes a first transducer for determining the height of the impact means above the testing station, a second transducer for determining the additional energy imparted by the supplemental energy-input means, and circuit means for deactivating the electromagnet when the impact means reaches the second position, as determined by the first and second transducers and the control means.

8. The invention of claim 1 wherein the supplemental energy-input means includes a spring and the apparatus includes further coupling means for engaging and compressing the spring upon movement of the impact means from the intermediate position toward the second position.

9. The invention of claim 8 wherein the guide means includes a generally tubular guide and said impact means includes an impact member loosely fitted within the generally tubular guide for relatively unrestrained movement between the first and second positions and free-fall between the intermediate and first positions.

10. The invention of claim 9 wherein the spring comprises a helical spring coextensive with a portion of the generally tubular guide, outside the generally tubular guide.

11. The invention of claim 10 wherein the spring is fixed in the apparatus relative to the generally tubular guide, and the further coupling means includes coupling members carried by the impact member for engaging the spring at the intermediate position.

12. The invention of claim 1 wherein the guide means includes a generally tubular guide and said impact means includes an impact member loosely fitted within the generally tubular guide for relatively unrestricted movement between the first and second positions.

13. The invention of claim 12 wherein the coupling means includes an electromagnet for coupling the impact means with the elevating means.

14. The invention of claim 13 wherein the control means includes a first transducer for determining the height of the impact means above the testing station, a second transducer for determining the additional energy imparted by the supplemental energy-input means, and circuit means for deactivating the electromagnet when the impact means reaches the second position, as determined by the first and second transducers and the control means.

15. The invention of claim 13 wherein the supplemental energy-input means includes a spring and the apparatus includes further coupling means for engaging and compressing the spring upon movement of the impact means from the intermediate position toward the second position.

16. The invention of claim 15 wherein the spring comprises a helical spring coextensive with a portion of the generally tubular guide, outside the generally tubular guide.

17. The invention of claim 16 wherein the spring is fixed in the apparatus relative to the generally tubular guide, and the further coupling means includes coupling members carried by the impact member for engaging the spring at the intermediate position.

18. The invention of claim 17 wherein the control means includes a first transducer for determining the height of the impact means above the testing station, a second transducer for determining the additional energy imparted by the supplemental energy-input means, and circuit means for deactivating the electromagnet when the impact means reaches the second position, as determined by the first and second transducers and the control means.

19. The invention of claim 1 wherein the prescribed location in the testing station includes a test plane and the holding means includes at least one holding member for locating at least a portion of the test specimen in said test plane.

20. The invention of claim 19 wherein the first position is at said test plane and the holding means includes a further holding member movable relative to said one holding member in a direction away from the second position for accommodating, between said holding members, a test specimen of one of various dimensions in said direction while maintaining said portion of the test specimen in said test plane and at said first position.

21. The invention of claim 20 wherein the guide means includes a generally tubular guide and said impact means includes an impact member loosely fitted within the generally tubular guide for relatively unrestricted movement between the first and second positions.

22. The invention of claim 21 wherein the supplemental energy-input means includes a spring and the apparatus includes further coupling means for engaging and compressing the spring upon movement of the impact means from the intermediate position toward the second position.

23. The invention of claim 21 wherein the coupling means includes an electromagnet for coupling the impact means with the elevating means.

24. The invention of claim 23 wherein the supplemental energy-input means includes a spring and the apparatus includes further coupling means for engaging and compressing the spring upon movement of the impact means from the intermediate position.

25. The invention of claim 24 wherein the control means includes a first transducer for determining the height of the impact means above the testing station, a second transducer for determining the additional potential energy imparted by the supplemental energy-input means, and circuit means for deactivating the electromagnet when the impact means reaches the second position, as determined by the first and second transducers and control means.

* * * * *